United States Patent [19]
Murata

[11] Patent Number: 6,019,737
[45] Date of Patent: Feb. 1, 2000

[54] GUIDE WIRE

[75] Inventor: Yukihiko Murata, Shizuoka, Japan

[73] Assignee: Terumo Kabushiki Kaisha, Tokyo, Japan

[21] Appl. No.: 09/050,891

[22] Filed: Mar. 31, 1998

[30] Foreign Application Priority Data

Mar. 31, 1997 [JP] Japan ...................................... 9-096502
Mar. 31, 1997 [JP] Japan ...................................... 9-096503

[51] Int. Cl.[7] ........................................................ A61B 5/00
[52] U.S. Cl. ............................................................. 600/585
[58] Field of Search .................................... 600/410, 414, 600/420, 423, 424, 431, 434, 585

[56] References Cited

U.S. PATENT DOCUMENTS

| | | | |
|---|---|---|---|
| 5,154,779 | 10/1992 | Ratner | 600/420 |
| 5,720,300 | 2/1998 | Fagan et al. | 128/772 |
| 5,817,017 | 10/1998 | Young et al. | 600/433 |

FOREIGN PATENT DOCUMENTS

| | | |
|---|---|---|
| 0 325 426 | 7/1989 | European Pat. Off. . |
| 0 701 835 | 3/1996 | European Pat. Off. . |
| 0 701 836 | 3/1996 | European Pat. Off. . |
| 0 702 976 | 3/1996 | European Pat. Off. . |
| 0 744 186 | 11/1996 | European Pat. Off. . |
| 2-5932 | 1/1990 | Japan . |
| 8-173543 | 7/1996 | Japan . |
| 8-173544 | 7/1996 | Japan . |
| 8-173545 | 7/1996 | Japan . |
| 8-509141 | 10/1996 | Japan . |
| 94/23782 | 10/1994 | WIPO . |
| 97/17622 | 5/1997 | WIPO . |

OTHER PUBLICATIONS

Bakker et al., "Visualization of Dedicated Catheters Using Fast Scanning Techniques with Potential for MR–Guided Vascular Interventions", *Magnetic Resonance in Medicine*, vol. 36, No. 6, Dec. 1996, pp. 816–820, SP000636871.

McKinnon et al., "Towards Visible Guidewire Antennas for Interventional MRK", *Proceedings of the Society of Magnetic Resonance*, 2nd Meeting, San Francisco, Aug. 6–12, 1994, vol. 3, No. Meeting 2, Aug. 6, 1994, p. 429, XP002059033.

*Primary Examiner*—Max Hindenburg
*Attorney, Agent, or Firm*—Burns, Doane, Swecker & Mathis, LLP

[57] ABSTRACT

A guide wire (1A) shown in FIG. 1 of an Embodiment of the present invention is constituted by a core member (2) and a coil (3) wound around an outer periphery of the core member (2) all around the length of the core member (2). Stopper members (4) and (5) are provided in both ends of the core member (2), respectively. At least either of the core member (2) and the coil (3), thin film thereon, or a thin plate placed thereon is constituted by an alloy containing a nickel of 45 wt % or more, an iron of 3 to 6 wt %, a chrome of 10 to 25 wt % and a molybdenum of 10 to 20 wt %, or a metal material having a magnetic susceptibility at a temperature close to a room temperature (about 10 to 40° C.) in an outer diametrical direction of preferably $0.5 \times 10^{-4}$ to $\mathbf{5.0 \times 10^{-4}}$. The guide wire (1A) of this kind generates an artifact 1 to 7 times an actual outer diameter on an MRI image photographed by a gradient echo method, thereby suitably recognized in a monitor image by the MRI.

7 Claims, 13 Drawing Sheets

GUIDE WIRE

BACKGROUND OF THE INVENTION

1. Field of the Invention

The present invention relates to a guide wire, for example, used for introducing various kinds of catheters.

2. Prior Art

In the case of inserting a catheter into an organism, a front end portion of the catheter is introduced by inserting the guide wire into a lumen of the catheter and operating this, so that a selection of branching a blood vessel can be smoothly and securely performed.

As a conventional guide wire, there has been known a guide wire which is constituted by a stainless steel or a superelastic alloy (Ni—Ti alloy).

In this case, since an insertion of the catheter within the organism is performed under an X-ray irradiation, an X-ray contrast characteristic is applied to the catheter.

Recently, in a medical field, an examination and a diagnosis are performed in accordance with a magnetic resonance imaging method (MRI). Due to a progress of the technology, it is also possible to insert the catheter and a guide wire into a body of a person to be examined while monitoring an image by MRI, thereby performing a medical activity such as an examination and a diagnosis.

In this case, the conventional guide wire constituted by a stainless steel is magnetized due to a material characteristic thereof and a work hardening generated during a wiring process. Therefore, the guide wire is placed in a strong magnetic field of the MRI, a large artifact (an image not existing) appears on an MRI monitor image due to an excess reaction, and the guide wire is recognized as ten times greater in diameter than an actual thickness. As a result, a position of the front end portion of the guide wire within the organism can not be accurately recognized, which might cause incorrect medical activities as mentioned above.

Further, the guide wire heated by a strong magnetizing effect of the MRI, may also cause incorrect medical activities as mentioned above or giving a bad influence to the organism.

On the contrary, in the conventional guide wire constituted by the superelastic alloy (Ni—Ti alloy), the artifact generated on the MRI monitor image appears in a smaller diameter than the actual size of the guide wire, so that it is hard to recognize a position of the front end portion of the guide wire in the organism.

SUMMARY OF THE INVENTION

An object of the present invention is to provide a guide wire which can be appropriately recognized on an MRI monitor image.

This object can be achieved by the invention mentioned below.

(1) A guide wire comprising a contrast portion that generates an artifact one to eight times an actual outer diameter on an MRI image photographed by a gradient echo method.

(2) A guide wire in which the contrast portion is present in at least a front end portion of the guide wire.

(3) A guide wire in which the contrast portion is made of an alloy containing a nickel of 40 wt % or more and an iron of 7 wt % or less.

(4) A guide wire in which the alloy further contains a chrome and a molybdenum.

(5) A guide wire in which the alloy contains a nickel of 45 wt % or more, an iron of 2 to 7, preferably 3 to 6 wt %, a chrome of 10 to 25 wt % and a molybdenum of 10 to 20 wt %.

(6) A guide wire comprising a core member and a coil disposed at least in an outer periphery of a front end portion of the core member, in which at least a part of the coil or the core member in a longitudinal direction of the guide wire constitutes the contrast portion.

(7) A guide wire in which the coil is constituted by a metal material having a magnetic susceptibility of $0.5 \times 10^{-4}$ to $5.0 \times 10^{-4}$ in an outer diametrical direction of the coil at a temperature close to a room temperature.

(8) A guide wire in which a plurality of ring members are used in place of the coil.

(9) A guide wire in which the core member is constituted by a metal material having a magnetic susceptibility of $0.5 \times 10^{-4}$ to $5.0 \times 10^{-4}$ in an outer diametrical direction of the coil at a temperature close to a room temperature.

(10) A guide wire comprising a coat layer for coating at least a part of the contrast material.

(11) A guide wire in which a thin film made of a ferromagnetic body is provided at least in a front end portion of a core member constituted by a feeble(low) magnetic body or a non-magnetic body.

(12) A guide wire in which the thin film constituted by a ferromagnetic body is a thin film constituted by a transition metal or an alloy containing a transition metal.

(13) A guide wire in which the thin film is formed by a vapor phase film forming method.

(14) A guide wire in which a thickness of the thin film is 0.001 to 2.5 µm.

(15) A guide wire in which the core member is constituted by a metal material having a magnetic susceptibility of $5.0 \times 10^{-4}$ or less in an outer diametrical direction of the coil at a temperature close to a room temperature.

(16) A guide wire comprising a coat layer for coating at least a part of the thin film.

(17) A guide wire in which the coat layer is constituted by an organic polymeric material.

(18) A guide wire in which an X-ray impermeable material is contained in the material constituting the coat layer.

(19) A guide wire comprising a core member and a contrast portion for magnetic resonance imaging method wherein said contrast portion comprising an alloy containing a nickel of 40 wt % or more and an iron of 7 wt % or less at least a distal portion of the guide wire.

(20) A guide wire as recited in the (19), wherein said alloy further contains a chrome and a molybdenum.

(21) A guide wire as recited in the (19) or (20), wherein said alloy contains a nickel of 45 wt % or more, an iron of 2 to 7 wt %, a chrome of 10 to 25 wt % and a molybdenum of 10 to 20 wt %.

(22) A guide wire as recited any one in the (19) to (21), wherein said contrast portion generating an artifact one to eight times an actual outer diameter on an MRI image photographed by a gradient echo method.

(23) A guide wire as recited in any one of the (19) to (22) wherein said contrast portion is positioned at least in an outer periphery of a front end portion of said core member.

(24) A guide wire as recited in any one of the (19) to (23) wherein said core member comprising a super elastic alloy.

DESCRIPTION OF THE PREFERRED EMBODIMENT

A guide wire in accordance with the present invention will be described in detail below with reference to a preferred embodiment shown in the attached drawings.

A guide wire of the present invention can be used for performing a medical activity such as an examination, a diagnosis and a treatment under the operation of a magnetic resonance imaging (MRI).

The guide wire of the invention has a contrast portion which generates an artifact 1 to 8 times an outer diameter of an actual guide wire on the MRI image photographed by a gradient echo method, more preferably an artifact 1.5 to 7.5 times the outer diameter of the actual guide wire, and further preferably an artifact 2 to 7 times the outer diameter of the actual guide wire. When the artifact is too large, it is hard to recognize the position of the guide wire within a body cavity, and when the artifact is too small, there is a case that it is hard to see the artifact on the MRI image by a spin echo method which corresponds to another photographing method of the MRI.

It is preferable that the contrast portion is present at least in a front end portion of the guide wire.

A concrete structure of the guide wire of the present invention is not particularly limited as far as the guide wire has the contrast portion including the characteristic mentioned above, and there is a case that the guide wire is basically formed by a rod member and there is a case that the guide wire is constituted by winding a coil around a part or all of the rod member. An embodiment of a preferred structure will be described below with reference to FIGS. 1 to 17. In this case, the description is given while considering a right portion in FIGS. 1 to 17 as "a basic end" and a left portion as "a front end". At a time of inserting the guide wire into the body, "the basic end" corresponds to an end to be inserted in the front end, and on the contrary, "the front end" corresponds to a front end inserted into the body.

Figure 1:
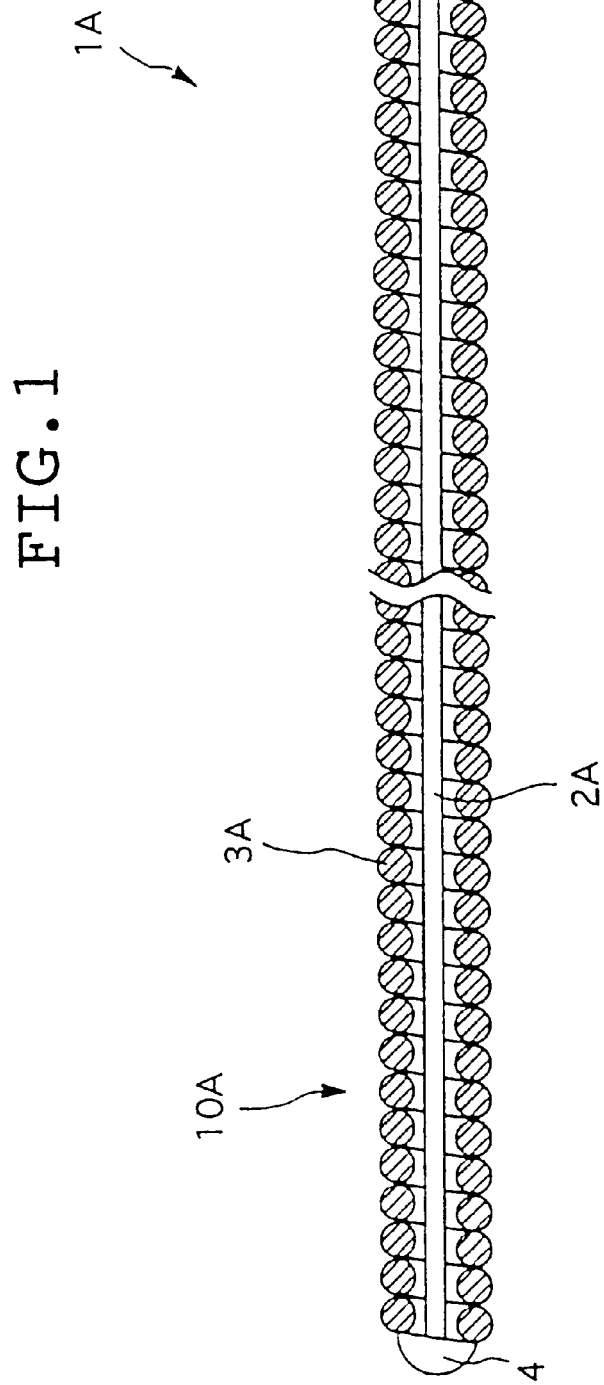
FIG. 1 is a vertical cross sectional view which shows an embodiment of a guide wire in accordance with the present invention.

FIG. 1 is a vertical cross sectional view which shows an embodiment of the guide wire in accordance with the present invention.

As shown in the drawing, a guide wire 1A, in accordance with the invention is constituted by a core member 2A and a coil 3A wound around an outer periphery all along the length of the core member 2A. The guide wire 1A has a flexibility as a whole, and has a suitable rigidity and elasticity in such a manner as to sufficiently effect a function as the guide wire.

Further, stopper members 4 and 5 are provided in both ends of the core member 2A in such a manner that the coil 3A would not move longitudinally with respect to the core member 2A.

The core member 2A and the coil 3A may be in contact with each other, in close contact with each other, or in apart from each other with a predetermined gap, however, in view of improving a flexibility (an elasticity) of the guide wire 1A, the latter is preferable.

In this case, in the illustrated embodiment, a cross sectional shape of a wire material constituting the coil 3A is a circular shape, however, the shape is not limited to this, and any other shapes may be employed, for example, an oval shape, a semi-circular shape, a semi-oval shape, a triangular shape, a polygonal shape such as a rectangular shape and a flat shape (a planner shape).

Further, the coil 3A may be wound in two or more layers.

Still further, the core member 2A may be formed as a multi-layered structure, a hollow structure and a structure formed by binding a plurality of core members, as is different from the illustrated embodiment.

In the guide wire 1A of this kind, at least either of the core member 2A and the coil 3A, or a part thereof forms a contrast portion and is constituted in such a manner as to generate an artifact 1 to 8 times an actual outer diameter on the MRI image photographed by the gradient echo method. Preferably, the contrast portion is formed by an alloy containing a nickel of 40 wt % or more and an iron of 7 wt % or less. More preferably, it is formed by an alloy further containing a chrome and molybdenum. Particularly, the alloy may contain a nickel of 45 wt % or more, an iron of 3 to 6 wt %, a chrome of 10 to 25 wt % and a molybdenum of 10 to 20 wt %, and may further contain a tungsten if necessary.

Further, in the guide wire 1A of this kind, at least either of the core member 2A and the coil 3A is constituted by a metal material having a magnetic susceptibility of preferably $0.5 \times 10^{-4}$ to $5.0 \times 10^{-4}$, and more preferably $1.0 \times 10^{-4}$ to $3.0 \times 10^{-4}$ in an outer diametrical direction at a temperature close to a room temperature (about 10 to 40° C.)

By using the alloy constituted by a specific component mentioned above or the metal material having the magnetic susceptibility (hereinafter, refer to "a low magnetic susceptibility metal material"), the artifact having the range mentioned above can be generated. Accordingly, in the guide wire 1A of this embodiment, a portion extending all around the length constitutes the contrast portion.

Here, the magnetic susceptibility is defined as follows.

Figure 6:
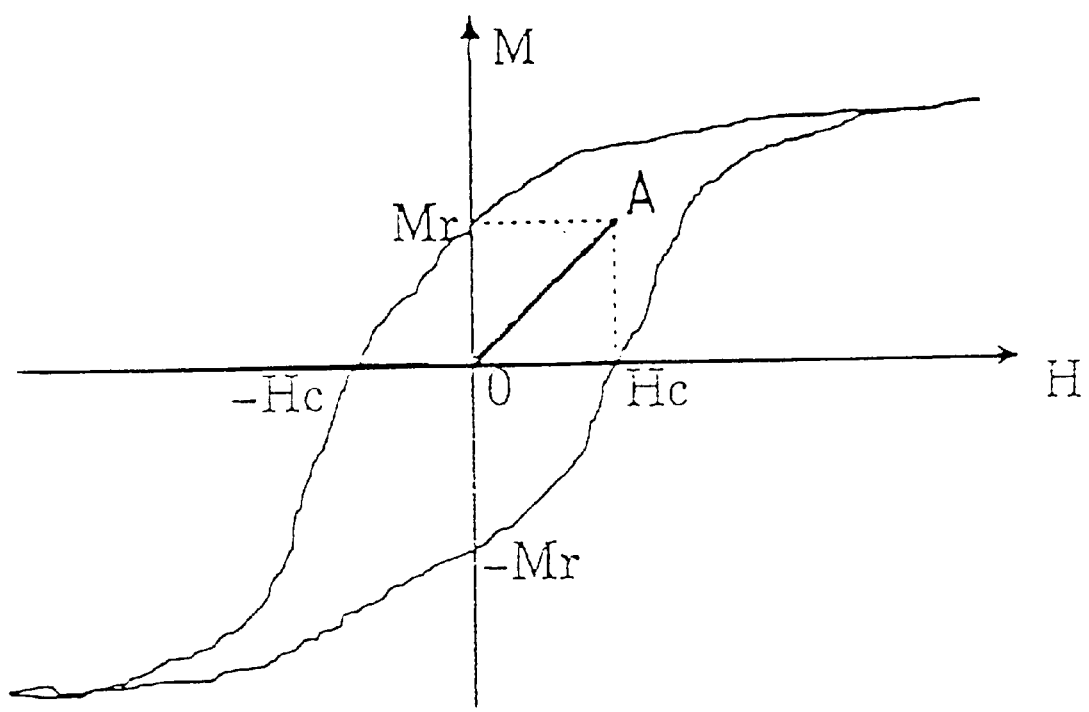
FIG. 6 is a graph which shows an MH magnetization curve.

In an MH magnetizing curve (a magnetic hysteresis curve) shown in FIG. 6, a magnetic susceptibility is an inclination of a straight line formed by connecting a point A having coordinates of a coercive force Hc (per unit volume [cm$^3$]) and a residual magnetization Mr with the origin 0.

The magnetic susceptibility X is expressed by the following formula:

Magnetic Susceptibility X=M (magnetization:unit [G])/H(magnetic field:unit [Oe])

=Mr [emu]/(volume [cm$^3$]×Hc[Oe])

A non-magnetic material (a non-magnetic body) and a feeble magnetic body (any of the metal material and the resin material can be employed) may be applied, in the case that either of the core member 2A or the coil 3A is not constituted by the specific alloy mentioned above or by the low magnetic susceptibility metal material.

An outer diameter of the guide wire 1A of this kind is not specifically limited, however, it is normally preferable to set an average outer diameter to be about 0.25 to 1.57 mm, and it is further preferable to set to about 0.4 to 0.97 mm.

In this case, for example, by forming the front end portion of the core member 2A in a taper shape an outer diameter of which is gradually reduced toward the front end direction, it may be structured that a rigidity (a bending rigidity and a torsion rigidity) in the front end portion 10A of the guide wire 1A is gradually reduced toward the front end direction. By constituting in this manner, the flexibility of the front end portion 10A can be improved and a higher safety can be secured while sufficiently maintaining a torque transmission performance, a inserting performance (a pushability) and an anti-kink performance (an anti-bending performance) of the guide wire 1A.

Figure 2:
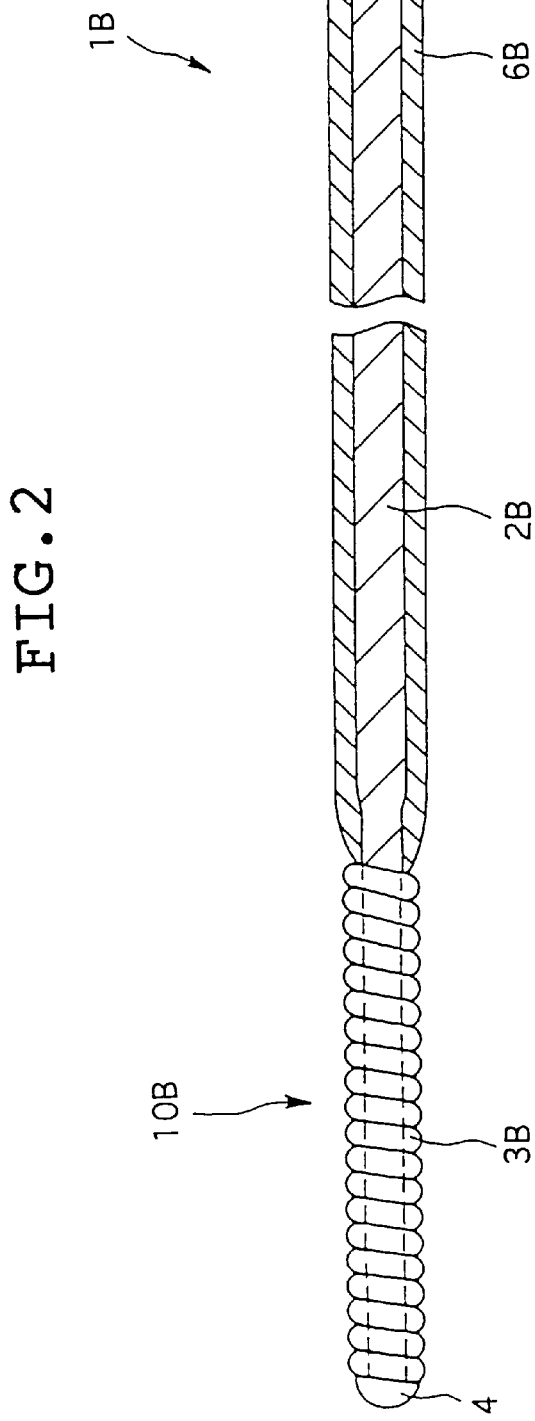
FIG. 2 is a vertical cross sectional view which shows another embodiment of a guide wire in accordance with the present invention.

FIG. 2 is a vertical cross sectional view which shows another embodiment of the guide wire in accordance with the present invention. A guide wire 1B shown in FIG. 2 will be described below in view of points different from the guide wire 1A, and the description with respect to the same matters will be omitted.

The guide wire 1B has a core member 2B having the same structure as that mentioned above, and a coil 3B having the same structure as that mentioned above is disposed only in a front end portion 10B of the guide wire 1B.

At least either of the core member 2B and the coil 3B is structured by the alloy constituted by the specific component mentioned above or the low magnetic susceptibility metal material, as in the same manner as that mentioned above. In this case, in the guide wire 1B in which the core member 2B is constituted by the specific alloy or the low magnetic susceptibility metal material, almost all the portion around the length thereof constitutes the contrast portion, and in the guide wire 1B in which only the coil 3B is constituted by the specific alloy or the low magnetic susceptibility metal material, only the front end portion 10B constitutes the contrast portion.

In an outer periphery of a portion close to the base end than the coil 3B of the core member 2B, a coat layer 6B is coated and formed. A suitable flexibility and strength can be obtained by forming the coat layer 6B, and further, an effect of making it possible to provide a coating layer made of a surface lubricant polymer can be obtained.

The coat layer 6B is preferably constituted by an organic polymeric material. As an organic polymeric material constituting the coat layer 6B, for example, there can be employed a polyolefin such as a polyethylene, a polypropylene and an ethylene-vinyl acetate copolymer, a polyester such as a polyethylene terephtalate and polybutylene terephtalate, various kinds of thermoplastic elastomer such as a polyvinyl chloride, polyvinylidene chloride, polystyrene, polyamide (for example, a nylon 6, a nylon 66, a nylon 11 and a nylon 12), a polyimide, a polyamide imide, a polycarbonate, a poly-(4-methyl pentene-1), an ionomer, an acrylic resin, a polymethyl methacrylate, an acrylonitrile-butadiene-styrene copolymer (ABS resin), an acrylonitrile-styrene copolymer (AS resin), a butadiene-styrene copolymer, a polyoxymethylene, a polyvinyl alcohol (PVA), a polyether, a polyether ketone (PEK), a polyether ether ketone (PEEK), a polyether imide, a polyacetal (POM), a polyphenylene oxide, a denaturation polyphenylene oxide, a polysulfon, a polyether sulfon, a polyphenylene sulfide, a polyarilate, an aromatic polyester (a liquid-crystal polymer), a polytetrafluoroethylene, a polyvinylidene fluoride, the other fluorocarbon type resin, a styrene type, a polyolefin type, a polyvinyl chloride type, a polyurethane type, a polyester type, a polyamide type, a polybutadiene type, a trans polyisoprene type, a fluorine-contained rubber type, a chlorinated polyethylene type and the like, an epoxy resin, a phenolic resin, a urea resin, a melamine resin, an unsaturated polyester, a silicone resin, a polyurethane or a copolymer mainly containing these materials, a blended material, and a polymer alloy, and the material mentioned above can be used as a single material or a combination of two or more kinds (for example, as a layered body having two or more layers).

Further, an X-ray impermeable material such as a barium sulfate, a bismuth oxide and a tungsten may be combined in the coated layer 6B as occasion demands in such a manner as to recognize the position even in the case of using the guide wire 1B under the X-ray illumination.

The coated layer 6B gives effects of protecting the core member 2B and a thin film 13B mentioned below, improving a slidability of the guide wire, and making it possible to form a coating layer of a surface lubricant polymer.

A thickness of the coated layer 6B is not particularly limited, however, it is generally preferable to set to be about 0.05 to 0.3 mm, and about 0.1 to 0.2 mm is more preferable.

Further, a thickness of the coated layer 6B is either even all around the coated layer 6B or different in accordance with a portion thereof. For example, a portion a thickness of which is gradually reduced or increased toward the front end direction may be included.

In this case, the coated layer 6B may be formed in such a manner as to coat an area of the front end portion 10B, that is, an outer periphery of the coil 3B. Further, the coated layer 6B may be formed only in the area of the front end portion 10B.

In the guide wires 1A and 1B mentioned above, a plurality of ring-like members (not shown) can be employed in place of the coils 3A and 3B. In this case, a material and a characteristic of the ring-like member may be set to be the same as those mentioned in the coils 3A and 3B.

Figure 3:
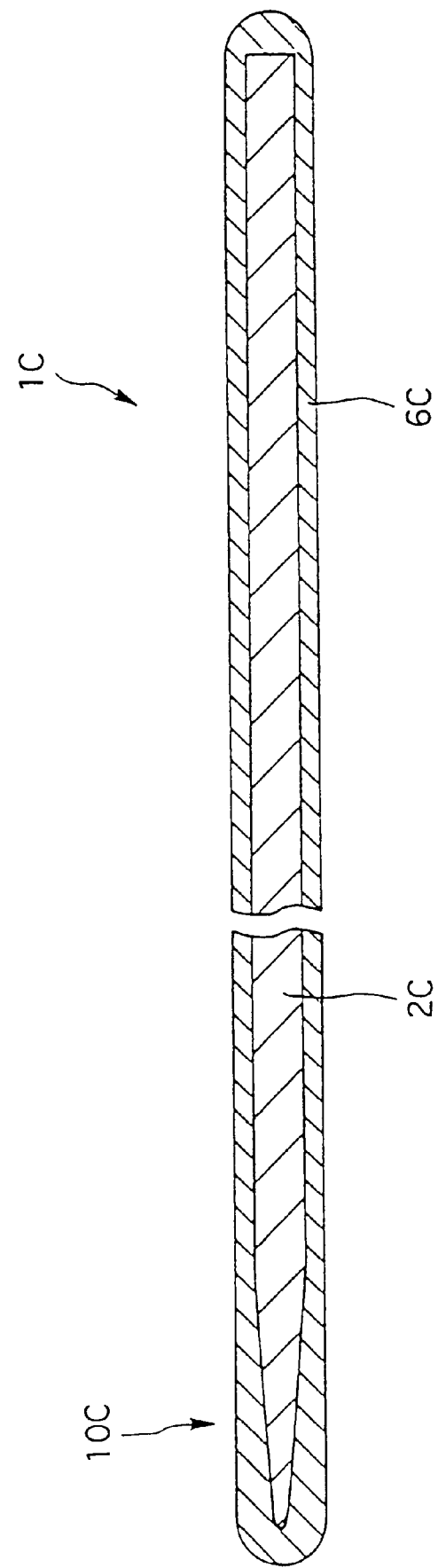
FIG. 3 is a vertical cross sectional view which shows the other embodiment of a guide wire in accordance with the present invention.

FIG. 3 is a vertical sectional view which shows the other embodiment of the guide wire in accordance with the invention. A guide wire 1C shown in FIG. 3 will be described below in view of points different from the guide wire 1B, and the description with respect to the same matters will be omitted.

The guide wire 1C has a core member 2C, and a coated layer 6C having the same structure as that mentioned above is formed in an outer periphery all around the length thereof.

The core member 2C is constituted by an alloy containing a nickel of 40 wt % or more and an iron of 7 wt % or less. More preferably, it is constituted by an alloy further containing a chrome and a molybdenum. Particularly, the alloy may contain a nickel of 45 wt % or more, an iron of 3 to 6 wt %, a chrome of 10 to 25 wt % and a molybdenum of 10 to 20 wt %, and may further contain a tungsten as occasion demands. Otherwise, the core member 2C is constituted by a metal material having a magnetic susceptibility at a temperature close to a room temperature (about 10 to 40° C.) and in the outer diametrical direction preferably of $0.5 \times 10^{-4}$ to $5.0 \times 10^{-4}$, more preferably of $0.5 \times 10^{-4}$ to $3.0 \times 10^{-4}$, and further preferably of $1.0 \times 10^{-4}$ to $2.8 \times 10^{-4}$.

By employing the alloy constituted by the specific components or the metal material (the low magnetic susceptibility metal material) having the specific magnetic characteristic, the artifact having the range mentioned above can be generated. Accordingly, in the guide wire 1C in accordance with this embodiment, the portion extending all around the length constitutes the contrast portion.

In this case, as shown in the drawing, it is preferable that the front end portion of the core member 2C is formed in a taper shape in which the outer diameter thereof is gradually reduced toward the front end direction. Accordingly, it can be structured such that a rigidity (a bending rigidity and a torsion rigidity) of the front end portion 10C of the guide wire 1C is gradually reduced toward the front end direction, thereby improving a flexibility of the front end portion 10C and securing higher safety while maintaining a torque transmitting performance, a pressing performance (a pushability) and an anti-kink performance (an anti-bending performance) of the guide wire 1C.

Figure 4:
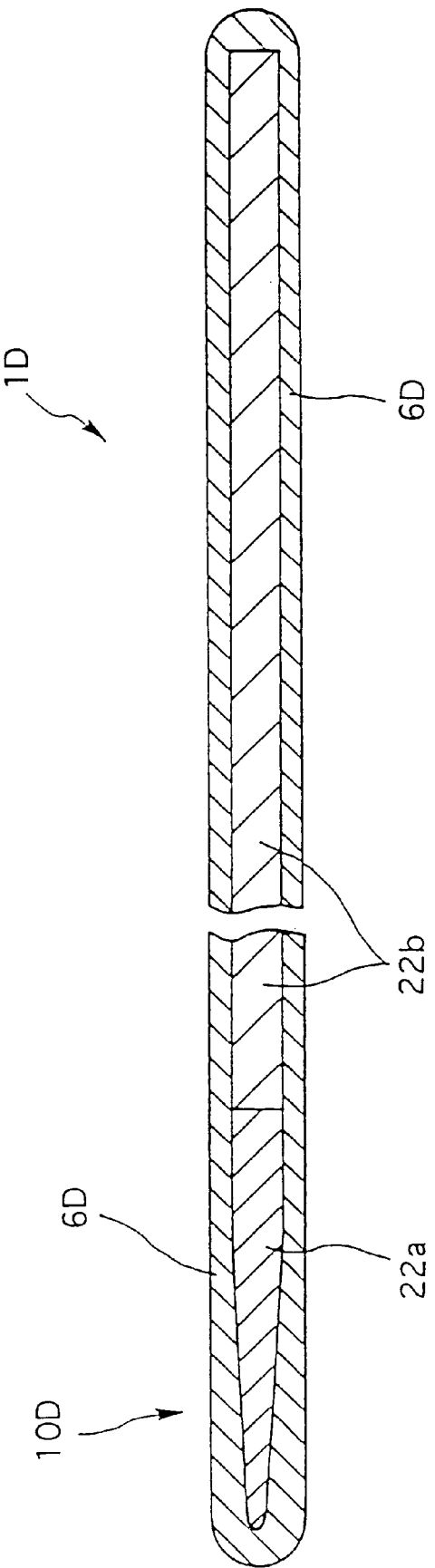
FIG. 4 is a vertical cross sectional view which shows further the other embodiment of a guide wire in accordance with the present invention.

FIG. 4 is a vertical sectional view which shows the other embodiment of the guide wire in accordance with the invention. A guide wire 1D shown in FIG. 4 will be described below in view of points different from the guide wire 1C, and the description with respect to the same matters will be omitted.

The guide wire 1D has the same structure as that of the guide wire 1C except that a core member structured by bonding a first core member 22a close to the front end and a second core member 22b close to the base end, for example, by welding, brazing or caulking is employed.

In this case, a component of the first core member 22a is different from a component of the second core member 22b, and at least the first core member 22a is constituted by the specific alloy or the low magnetic susceptibility metal material. Accordingly, in the guide wire 1D in accordance with this embodiment, the portion close to the front end portion 10D constitutes the contrast portion.

Further, each of the first core member 22a and the second core member 22b may be constituted by the alloy composed of the specific components mentioned above or the low magnetic susceptibility metal material.

The first core member 22a and the second core member 22b may be bonded by using a metal pipe. Preferably, the materials constituted the pipe member and the first core member may be the same.

Figure 5:
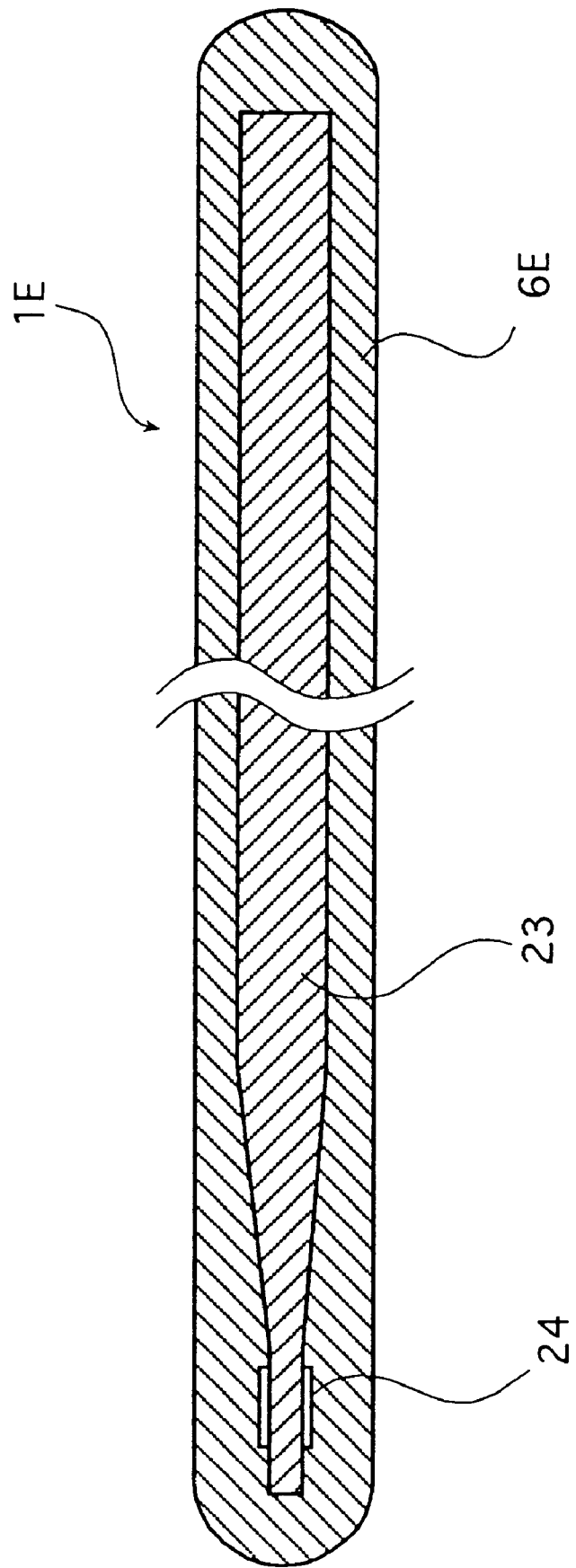
FIG. 5 is a vertical cross sectional view which shows further the other embodiment of a guide wire in accordance with the present invention.

FIG. 5 is a vertical sectional view which shows the other embodiment of the guide wire in accordance with the present invention. A guide wire 1E shown in FIG. 5 will be described below in view of points different from the guide wire 1D, and the description with respect to the same matters will be omitted.

Super elastic alloy (Ni—Ti alloy) which is thought to have the best property as a guide wire is used for the material constituted the core member 23 of the guide wire 1E, and its front end portion is tapered to thinner diameter in the same manner as the guide wire 1C already mentioned.

As described above the artifact of Ni—Ti alloy generated on the MRI monitor image appears smaller than it's actual size, so the thinned front end is especially hard to be recognized.

In this embodiment, the MRI marker 24 being positioned in the front end portion of the core member 23 is constituted by an alloy containing a nickel of 40 wt % or more and an iron of 7 wt % or less. More preferably, it is constituted by an alloy further containing a chrome and a molybdenum. Particularly, the alloy may contain a nickel of 45 wt % or more, an iron of 3 to 6 wt %, a chrome of 10 to 25 wt % and a molybdenum of 10 to 20 wt %, and may further contain a tungsten as occasion demands. Otherwise, the MRI marker 24 is constituted by a metal material having a magnetic susceptibility at a temperature close to a room temperature (about 10 to 40° C.) and in the outer diametrical direction preferably of $0.5 \times 10^{-4}$ to $5.0 \times 10^{-4}$, more preferably of $0.5 \times 10^{-4}$ to $3.0 \times 10^{-4}$, and further preferably of $1.0 \times 10^{-4}$ to $2.8 \times 10^{-4}$.

The MRI marker 24 is constituted by bonding or caulking thin plate processed from above mentioned specific material to the front end portion of the core member 23. Thus the place of the MRI marker constitutes the above mentioned contrast portion of the guide wire 1E in this embodiment. Guide wire 1E may also have the same coated layer 6E on entire or a portion of the surface as mentioned in the guide wire 1C or 1D.

The MRI marker 24 has a thickness of 20 to 200 μm, more preferably of 50 to 100 μm, and the width of the marker 24 in the axial direction on the guide wire is preferably 0.2 to 10 mm, more preferably of 0.5 to 5 mm.

Figure 11:
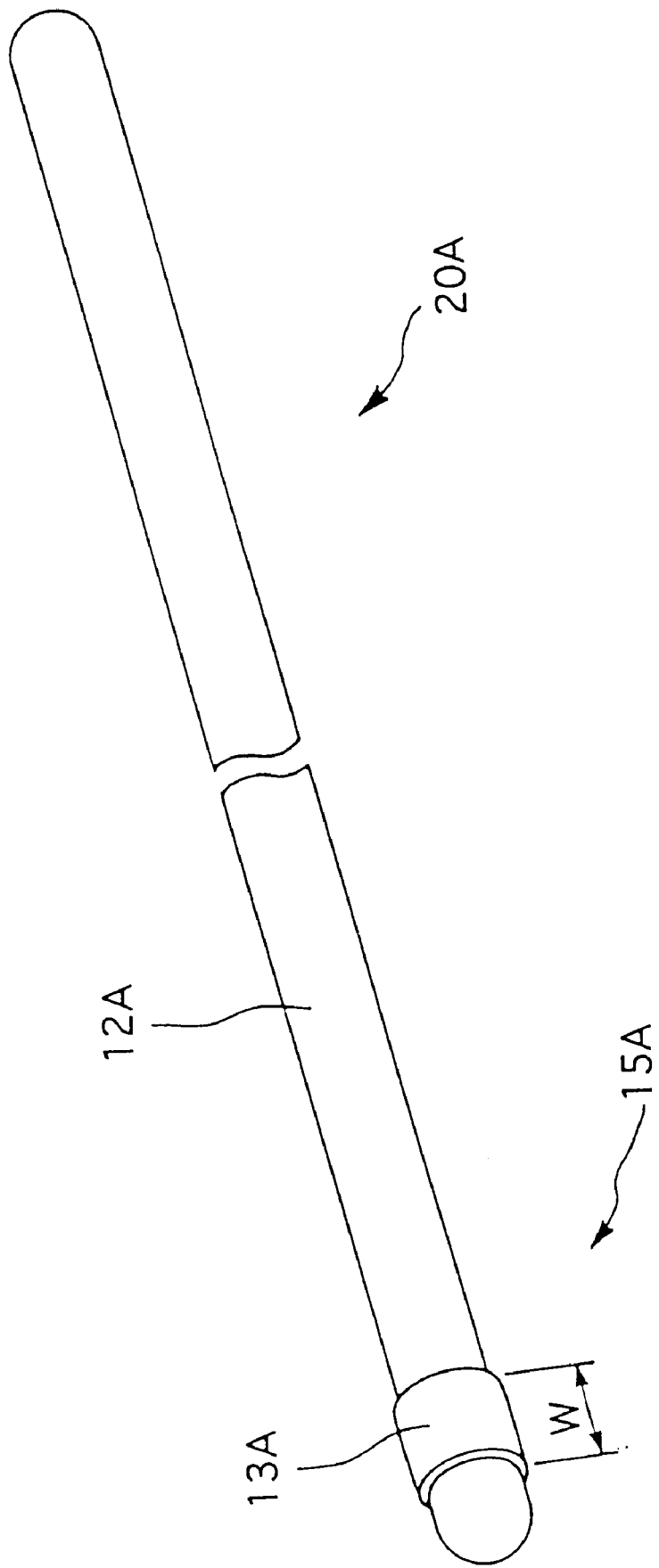
FIG. 11 is a stereoscopic view which shows an embodiment of a guide wire in accordance with the present invention.

A guide wire 20A in accordance with the invention as shown in FIG. 11 is used for performing a medical activity such as a examination, a diagnosis and a treatment under an operation of a magnetic resonance imaging apparatus (MRI apparatus).

The guide wire 20A is provided with a core member 12A having an elasticity. In the case of this embodiment, the core member 12A is constituted by a core member comprising a solid wire material. The core member 12A corresponds to a portion carrying a rigidity of the guide wire 20A, and has an appropriate rigidity and elasticity.

The core member 12A restricts an increase of the artifact on the MRI image, and has a contrast portion making the artifact a range of 1 to 8 times an actual outer diameter further by disposing a thin film 13A mentioned below. A material of the core member 12A is preferably a feeble magnetic body or a non-magnetic body. Concretely speaking, for example, a metal material such as a superelastic alloy (Ni—Ti alloy) and Ni—Cr—Mo alloy can be exemplified.

Further, in the case of constituting the core member 12A by the metal material, the metal material is structured such that the magnetic susceptibility at a temperature close to a room temperature (about 10 to 40° C.) in the outer diametrical direction is preferably $5.0\times10^{-4}$ or less, more preferably about $0.5\times10^{-4}$ to $4.0\times10^{-4}$, and further preferably about $1.0\times10^{-4}$ to $3.5\times10^{-4}$.

An artifact mentioned below can be effectively generated by using the metal material having the magnetic characteristic mentioned above (the low magnetic susceptibility metal material) to all or a part of the core member 12A.

A diameter of the core member 12A is not specifically limited, however, it is generally preferable to set it to be about 0.25 to 1.57 mm, and more preferable to set to be about 0.40 to 0.97 mm.

In this case, in the illustrated embodiment, the diameter of the core member 12A is substantially constant all around the length thereof, however, the structure is not limited to this, for example, it may be formed in a taper shape an outer diameter of which is gradually reduced toward the front end direction in the front end portion of the core member 12A. In accordance with this structure, a rigidity (a bending rigidity and a torsion rigidity) of the front end portion 15A of the guide wire 20A is gradually reduced toward the front end direction. As a result, a flexibility of the front end portion 15A can be improved and a higher safety can be secured while sufficiently maintaining a torque transmitting performance, a pressing performance (a pushability) and an anti-kink characteristic (an anti-bending characteristic) of the guide wire 20.

Further, the core member 12A may be constituted by a combination of two or more different materials. For example, the base end portion and the front end portion of the core member 12A are respectively constituted by a first material and a second material different from each other, and the rigidity of the first material may be set to be higher than the rigidity of the second material. In this case, the first material and the second material can be bonded, for example, by welding, brazing or caulking.

The first material and the second material may be bonded by using a metal pipe. Preferably, the materials constituted the pipe member and the first or second material be the same.

The thin film 13A is formed in the front end portion of the core member 12A in such a manner as to coat the outer periphery thereof. The thin film 13A is preferably constituted by a ferromagnetic body. Concretely speaking, for example, a transition metal such as an iron, a nickel and a cobalt or an alloy containing these components (for example, a stainless steel) can be exemplified. An artifact mentioned below can be obtained on the MRI image by providing the thin film 13A made of the material.

The thin film 13A can be formed, for example, by various kinds of plating methods (a liquid phase film forming method) such as an electroplating, a hot dipping and an electroless plating, various kinds of vapor phase film forming methods such as a vacuum evaporation, a sputtering, an ion plating, a CVD and a PVD, and particularly it is preferable to be formed by the vapor phase film forming methods mentioned above. In the thin film 13A formed by the methods of this kinds, an orientation characteristic of an atomic arrangement is changed during a process of a film growth, so that even in the case of the ferromagnetic body, an appropriate artifact mentioned below can be generated.

The thickness of the thin film 13A is not particularly limited, however, it is generally preferable to set it to be 0.001 to 2.5 $\mu$m, and it is more preferable to set it to be 0.01 to 1.0 $\mu$m.

The thin film 13A in accordance with this embodiment is formed in such a manner as to coat all the periphery of an outer periphery of the front end portion of the core member 12A in a web-like manner, that is, in a ring shape. In this case, a width W of the thin film 13A is not particularly limited, however, is preferably set to be about 0.2 to 10 mm in order to obtain a suitable artifact, and is more preferably set to be about 0.5 to 5 mm.

In this case, a pattern of forming the thin film 13A is not limited to the illustrated structure, however, various patterns such as a pattern formed along a longitudinal direction of the core member 12A in a linear and web-like manner, a pattern formed in a spiral manner or a pattern combining these patterns and the ring-like pattern mentioned above can be employed.

Further, the thin film 13A is not limited to the structure having a single layer, however, may be constituted by a plurality of layers (a multi-layer thin film).

The guide wire 20A has a contrast portion generating an artifact of 1 to 8 times an outer diameter of the actual guide wire on the MRI image photographed by a gradient echo method, more preferably an artifact of 1.5 to 7.5 times and further preferably an artifact 2 to 7 times. When the artifact is too large, it is hard to recognize a position of the guide wire within the body cavity, and when it is too small, there is a case that it is hard to see the artifact on the MRI image by the spin echo method corresponding to the other photographing method of the MRI.

In the case of this embodiment, the contrast portion becomes the front end portion 15A of the guide wire 20A, that is, a portion close to the portion in which the thin film 13A is formed.

The appropriate artifact of this kind can be suitably adjusted in accordance with various conditions such as a material constituting the core member 12A, a composition of the thin film 13A, a thickness and a width.

Figure 12:
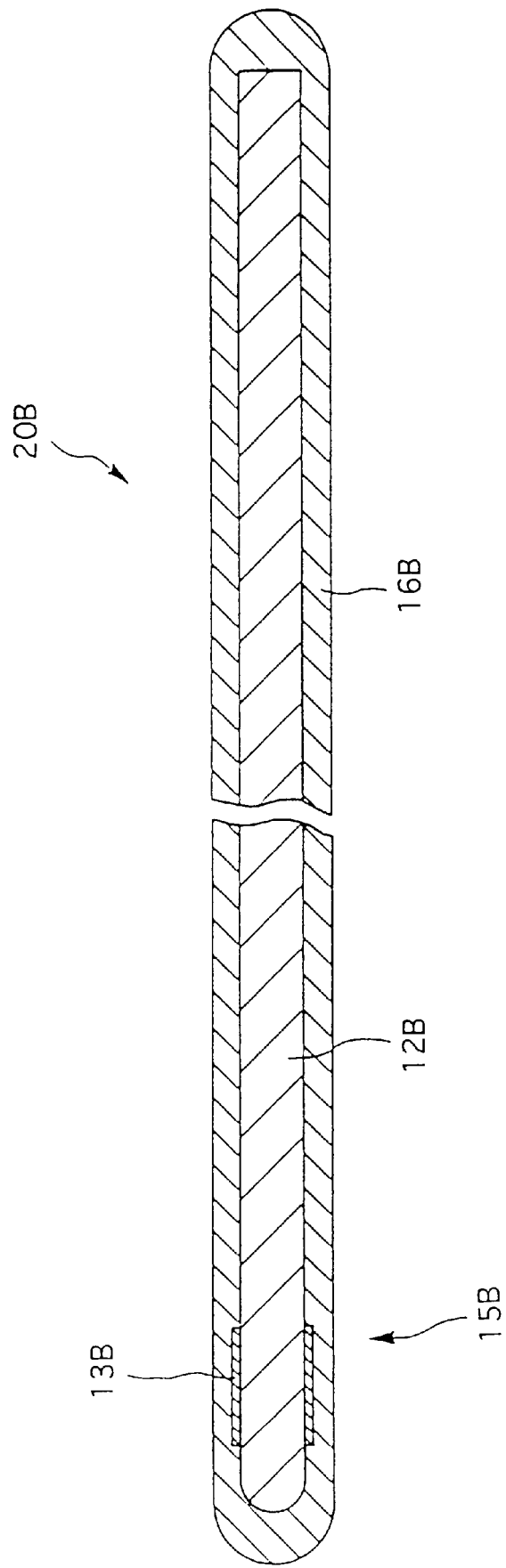
FIG. 12 is a vertical cross sectional view which shows another embodiment of a guide wire in accordance with the present invention.

FIG. 12 is a vertical sectional view which shows the other embodiment of the guide wire in accordance with the invention. A guide wire 20B shown in the drawing has a coated layer 16B, and the other structure is the same as that mentioned above. A description will be given below in view of the different points.

The coated layer 16B is coated and formed in an outer periphery extending substantially all around the length of the core member 12A. The coated layer 16B is preferably constituted by an organic polymeric material.

A material constituting the coated layer 16B is the same as that of the coated layer mentioned above.

A thickness of the coated layer 16B is not particularly limited, however, a thickness (an average thickness) of about 0.05 to 0.3 mm is preferable and a thickness of about 0.1 to 0.2 mm is more preferable.

Further, a thickness of the coated layer 16B may be either constant all around the coated layer 16 or different in correspondence to portions.

In this case, the coated layer 16B is not limited to a single layer as illustrated, however, may be a structure constituted by piling a plurality of layers.

In the guide wire 20B having the structure mentioned above, the artifact mentioned above is generated in the front end portion (the contrast portion) 15B.

Figure 13:
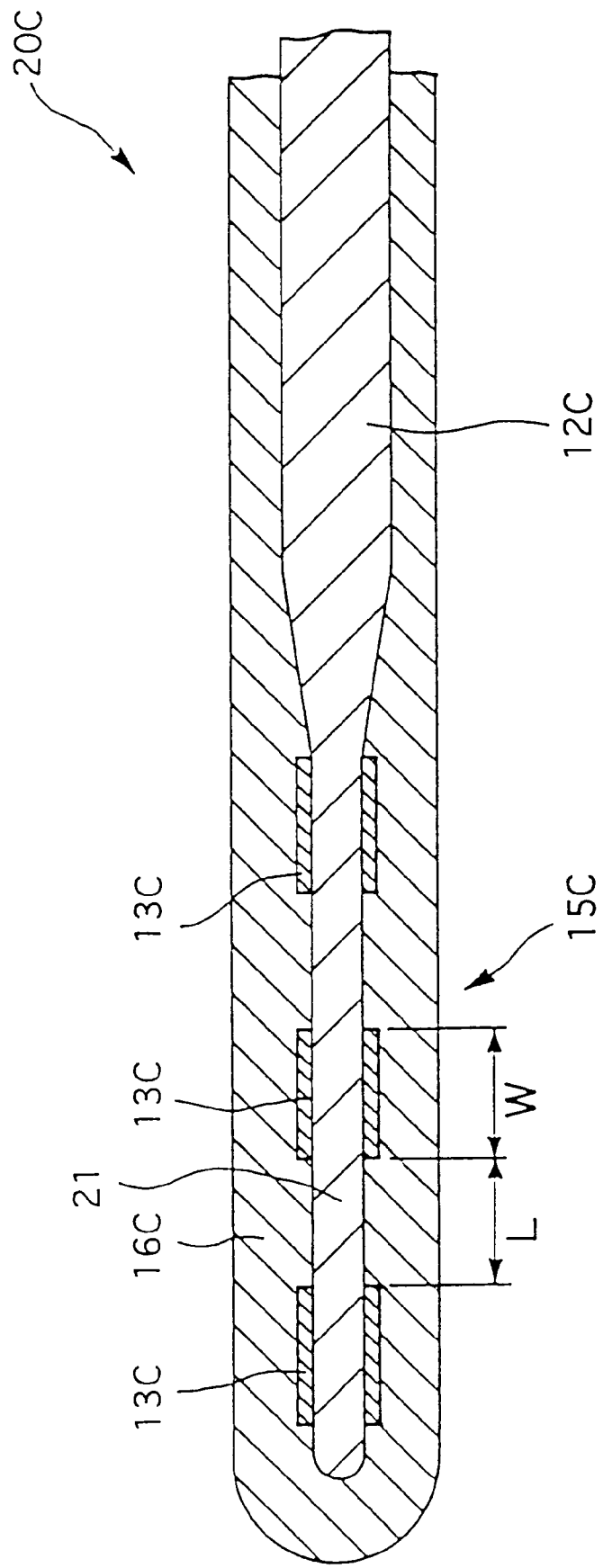
FIG. 13 is a vertical cross sectional view which shows a front end portion of the other embodiment of a guide wire in accordance with the present invention in an enlarged scale.

FIG. 13 is a vertical cross sectional view which shows a front end portion of the other embodiment of the guide wire in accordance with the invention in an enlarged manner. In a guide wire 20C shown in the drawing, a front end portion of the core member 12A is made a narrow diameter, and the coated layer 16C is made thick in the front end portion 15C so as to make an outer diameter of the guide wire constant, so that there are differences in comparison with the guide wire 20B in view of a point that the front end portion 15C is softened and a pattern of forming the thin film 13C, and the other points than those are the same. A description will be given below in view of the different points.

The guide wire 20C shown in FIG. 13 is structured such that a plurality of ring-like thin films 13C each having the same structure as that mentioned above are formed along a longitudinal direction of the guide wire 20C at a predetermined interval in an outer periphery of the front end narrow diameter portion 21 of the core member 12A. In this case, a width W of the thin film 13C is preferably about 1 mm to 5 mm, and a distance L of a gap between the adjacent thin films 13C is preferably about 1 mm to 5 mm.

In the guide wire 20C having the above structure, the artifact mentioned above is generated in the front end portion (the contrast portion) 15C.

The guide wire in accordance with the invention has been described above with reference to the respective embodiments, however, it is a matter of course that the guide wire of the invention is not limited to these structures.

For example, the core member is not limited to the solid wire material (the core material) as illustrated, however, may be a structure in which all or a part thereof is hollow. Further, the core member may be constituted by a structure binding a plurality of wire materials, a structure having a multi-layered pipe, a structure having a coil wound around the wire material (the core member), a coil itself, or an optional combination among them.

EXAMPLES

Concrete embodiments of the invention will be described in detail below.

Example 1

The guide wire shown in FIG. 1 is manufactured. Each of the conditions of the guide wire is as follows.

TOTAL LENGTH OF GUIDE WIRE: 1500 mm

OUTER DIAMETER (AVERAGE) OF GUIDE WIRE: 0.89 mm

MATERIAL CONSTITUTING CORE MEMBER: LOW MAGNETIC SUSCEPTIBILITY METAL MATERIAL M1 (COMPOSITION IS SHOWN AS FOLLOWS)

MAGNETIC SUSCEPTIBILITY OF MATERIAL CONSTITUTING CORE MEMBER: $1.36 \times 10^{-4}$ OUTER DIAMETER (AVERAGE) OF CORE MEMBER: 0.3 mm

ASPECT OF COIL: 1 GROOVE 1 LAYER CLOSE WINDING

MATERIAL CONSTITUTING COIL: SUPERELASTIC ALLOY (Ni—Ti ALLOY)

DIAMETER OF COIL WIRE MATERIAL: 0.15 mm

Example 2

The guide wire having the same structure as that of the Example 1 except that the material constituting the core member is set to be the low magnetic susceptibility metal material M2 mentioned below (magnetic susceptibility: $1.63 \times 10^{-4}$) is manufactured.

Example 3

The guide wire having the same structure as that of the Example 1 except that the material constituting the core member is set to be the superelastic alloy (Ni—Ti alloy) and the material constituting the coil is set to be the low magnetic susceptibility metal material M1 (magnetic susceptibility: $1.36 \times 10^{-4}$) is manufactured.

Example 4

The guide wire having the same structure as that of the Example 1 except that the material constituting the core member is set to be the superelastic alloy (Ni—Ti alloy) and the material constituting the coil is set to be the low magnetic susceptibility metal material M2 (magnetic susceptibility: $1.63 \times 10^{-4}$) is manufactured.

Example 5

The guide wire shown in FIG. 2 is manufactured. Each of the conditions of the guide wire is as follows.

TOTAL LENGTH OF GUIDE WIRE: 1500 mm

OUTER DIAMETER (AVERAGE) OF GUIDE WIRE: 0.89 mm

MATERIAL CONSTITUTING CORE MEMBER: SUPERELASTIC ALLOY (Ni—Ti ALLOY)

OUTER DIAMETER (AVERAGE) OF CORE MEMBER: 0.5 mm

ASPECT OF COIL: 1 GROOVE 1 LAYER CLOSE WINDING

AREA OF FORMING COIL: RANGE FROM FRONT END OF GUIDE WIRE TO 50 mm

MATERIAL CONSTITUTING COIL: LOW MAGNETIC SUSCEPTIBILITY METAL MATERIAL M1

MAGNETIC SUSCEPTIBILITY OF MATERIAL CONSTITUTING COIL: $1.36 \times 10^{-4}$

DIAMETER OF COIL WIRE MATERIAL: 0.15 mm

COMPOSITION OF COATED LAYER: POLYURETHANE

THICKNESS OF COATED LAYER: 0.2 mm

Example 6

The guide wire having the same structure as that of the Example 5 except that the material constituting the coil is set to be the low magnetic susceptibility metal material M2 (magnetic susceptibility: $1.63 \times 10^{-4}$) is manufactured.

Example 7

The guide wire having the same structure as that of the Example 5 except that the material constituting the core member is set to be the low magnetic susceptibility metal material M1 (magnetic susceptibility: $1.36 \times 10^{-4}$) is manufactured.

Example 8

The guide wire having the same structure as that of the Example 5 except that the material constituting the core member is set to be the low magnetic susceptibility metal material M2 (magnetic susceptibility: $1.63 \times 10^{-4}$) and the material constituting the coil is set to be the low magnetic susceptibility metal material M2 (magnetic susceptibility: $1.63 \times 10^{-4}$) is manufactured.

Example 9

The guide wire shown in FIG. 3 is manufactured. Each of the conditions of the guide wire is as follows.

TOTAL LENGTH OF GUIDE WIRE: 1500 mm

OUTER DIAMETER (AVERAGE) OF GUIDE WIRE: 0.89 mm

MATERIAL CONSTITUTING CORE MEMBER: LOW MAGNETIC SUSCEPTIBILITY METAL MATERIAL M3 (having the same composition as M1)

MAGNETIC SUSCEPTIBILITY OF MATERIAL CONSTITUTING CORE MEMBER: $2.1 \times 10^{-4}$ OUTER DIAMETER (AVERAGE) OF CORE MEMBER: 0.5 mm (NARROW DIAMETER PORTION OF FRONT END: 0.16 mm)

COMPOSITION OF COATED LAYER: POLYURETHANE

THICKNESS OF COATED LAYER: 0.2 mm

Example 10

The guide wire having the same structure shown in FIG. 4 is manufactured. Each of the conditions of the guide wire is as follows.

TOTAL LENGTH OF GUIDE WIRE: 1500 mm

OUTER DIAMETER (AVERAGE) OF GUIDE WIRE: 0.89 mm

MATERIAL CONSTITUTING FIRST CORE MEMBER (CLOSE TO FRONT END): LOW MAGNETIC SUSCEPTIBILITY METAL MATERIAL M3

MAGNETIC SUSCEPTIBILITY OF MATERIAL CONSTITUTING FIRST CORE MEMBER: $2.1 \times 10^{-4}$ MATERIAL CONSTITUTING SECOND CORE MEMBER (CLOSE TO BASE END): SUPERELASTIC ALLOY (Ni—Ti ALLOY)

METHOD OF BONDING FIRST AND SECOND CORE MEMBERS: WELDING

OUTER DIAMETER (AVERAGE) OF CORE MEMBER: 0.5 mm

COMPOSITION OF COATED LAYER: POLYURETHANE

THICKNESS OF COATED LAYER: 0.2 mm

Example 11

The guide wire shown in FIG. 5 is manufactured. Each of the conditions of the guide wire is as follows.

TOTAL LENGTH OF GUIDE WIRE: 1800 mm

OUTER DIAMETER (AVERAGE) OF GUIDE WIRE: 0.89 mm

MATERIAL CONSTITUTING CORE MEMBER: SUPERELASTIC ALLOY (Ni—Ti ALLOY)

OUTER DIAMETER (IN MAIN PORTION) OF CORE MEMBER: 0.5 mm

MATERIAL CONSTITUTING OF MRI MARKER: LOW MAGNETIC SUSCEPTIBILITY METAL MATERIAL M1

MAGNETIC SUSCEPTIBILITY OF MATERIAL CONSTITUTING MRI: $1.36 \times 10^{-4}$

DIAMETER OF MRI MARKER: 2 mm width, 80 μm thickness

METHOD OF FORMING MRI MARKER: CAULKING

COMPOSITION OF COATED LAYER: POLYURETHANE

THICKNESS OF COATED LAYER: 0.2 mm (IN MAIN PORTION)

Compositions of the low magnetic susceptibility metal materials M1 and M2 are as follows:

[LOW MAGNETIC SUSCEPTIBILITY METAL MATERIAL M1]
 Cr: 21.5 wt %
 Mo: 13.7 wt %
 W : 3.0 wt %
 Fe: 3.9 wt %
 Co: 0.7 wt %
 Mn: 0.17 wt %
 Si: 0.02 wt %
 Ni: the remainder

[LOW MAGNETIC SUSCEPTIBILITY METAL MATERIAL M2]
 Cr: 14.7 wt %
 Mo: 15.4 wt %
 W : 3.1 wt %
 Fe: 5.6 wt %
 Co: 1.0 wt %
 Mn: 0.6 wt %
 Si: 0.05 wt %
 Ni: the remainder Comparative Example 1

The guide wire having the same structure as that of the Example 9 except that the material constituting the core member is set to be a stainless steel (SUS304, magnetic susceptibility: $15.23 \times 10^{-4}$) is manufactured.

Comparative Example 2

The guide wire having the same structure as that of the Example 9 except that the material constituting the core member is set to be a Ni-49 wt % Ti alloy is manufactured.

<Experiment>

With respect to the case of placing each of the guide wires in accordance with the Examples 1 to 11 and the comparative Examples 1 and 2 into a water, an MRI image thereof is monitored by using an MRI (manufactured by GE MEDICAL CO., LTD) and photographing by a gradient echo method.

Figure 7:
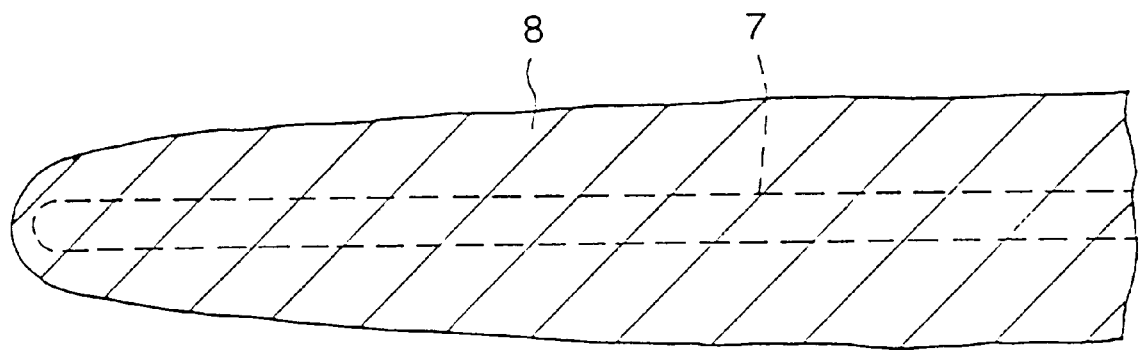
FIG. 7 is a schematic view which shows an outer appearance of a guide wire and a shape of an artifact of a guide wire on an MRI image in accordance with the present invention.

In each of the guide wires (the contrast portion is present substantially all around the length of the guide wire) in accordance with the Examples 1 to 4 and 7 to 9, a contour 7 of the actual guide wire (a dot line in FIG. 7) and an artifact 8 of the guide wire present on the MRI image (a solid line in FIG. 7) become shapes shown in FIG. 7 (schematically shown).

Figure 8:
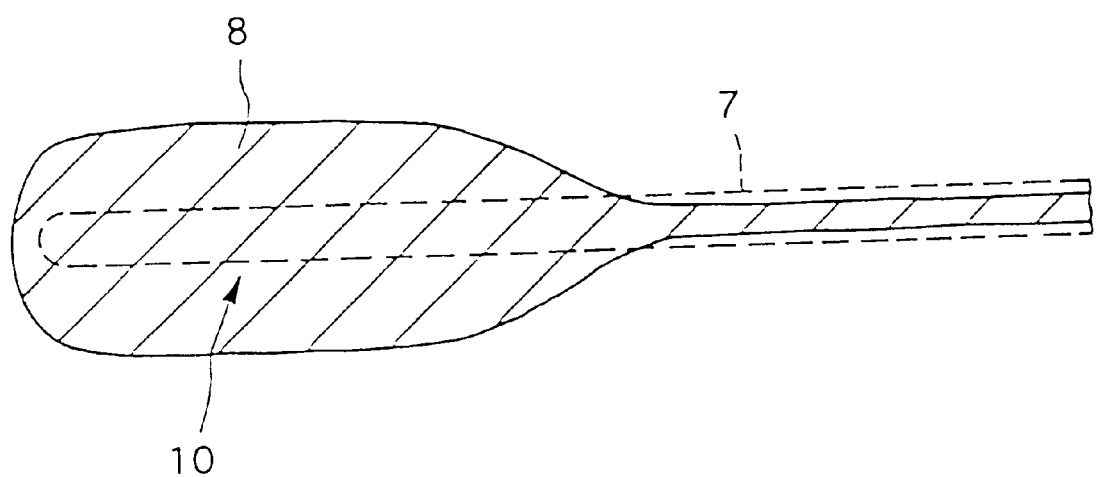
FIG. 8 is a schematic view which shows an outer appearance of a guide wire and a shape of an artifact of a guide wire on an MRI image in accordance with the present invention.

Further, in each of the guide wires (the contrast portion is present in the front end portion of the guide wire) in accordance with the Examples 5, 6, 10 and 11, the contour 7 of the actual guide wire (a dot line in FIG. 8) and the artifact 8 of the guide wire present on the MRI image (a solid line in FIG. 8) become shapes shown in FIG. 8 (schematically shown).

Figure 9:
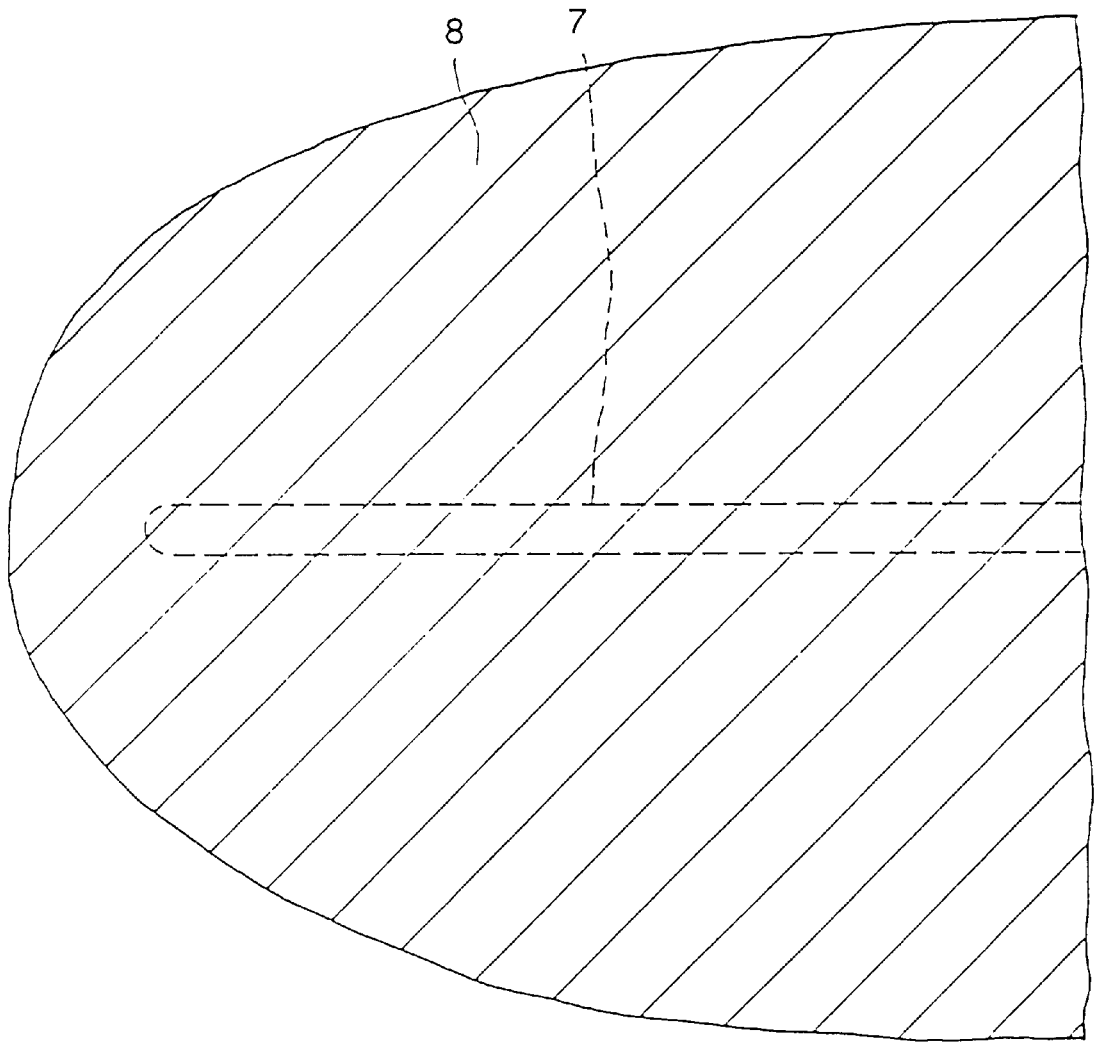
FIG. 9 is a schematic view which shows an outer appearance of a guide wire and a shape of an artifact of a guide wire on an MRI image in accordance with a comparative example.

On the contrary, in the guide wires in accordance with the comparative Example 1, the contour 7 of the actual guide wire (a dot line in FIG. 9) and the artifact 8 of the guide wire present on the MRI image (a solid line in FIG. 9) become shapes shown in FIG. 9 (schematically shown).

Figure 10:
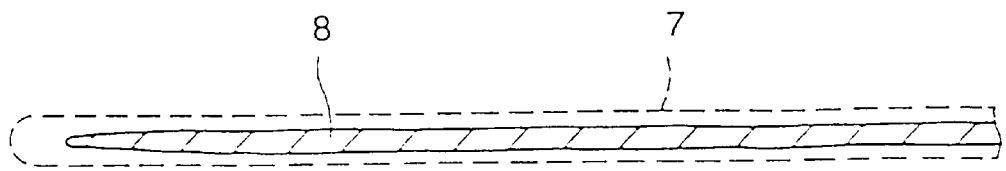
FIG. 10 is a schematic view which shows an outer appearance of a guide wire and a shape of an artifact of a guide wire on an MRI image in accordance with a comparative example.

Further, in the guide wires in accordance with the comparative Example 2, the contour 7 of the actual guide wire (a dot line in FIG. 10) and the artifact 8 of the guide wire present on the MRI image (a solid line in FIG. 10) become shapes shown in FIG. 10 (schematically shown). In this case, the artifact is very unclear and is hard to be recognized.

A magnification (an average value in each portion) of the artifact with respect to the actual outer diameter of the contrast portion in the guide wire is measured from the MRI image, so that the following results can be obtained.

Example 1: 2.4 times

Example 2: 3.4 times

Example 3: 3.4 times

Example 4: 4.4 times

Example 5: 3.4 times

Example 6: 4.4 times

Example 7: 4.0 times

Example 8: 5.6 times

Example 9: 1.3 times

Example 10: 1.3 times

Example 11: 2.6 times

Comparative Example 1: 25.6 times

Comparative Example 2: 0.5 times (front end portion 0.2 times)

Due to the results mentioned above, in each of the guide wires in accordance with the Examples 1 to 11, a position of the guide wire, particularly a position of the front end portion and a shape of the guide wire can be more accurately understood in the monitor image of the MRI.

In comparison with this, in the guide wire in accordance with the comparative Example 1, the artifact appears significantly greater than the actual outer diameter of the guide wire, and in the guide wire in accordance with the comparative Example 2, the image of the guide wire is unclear, so that in any of the cases, the position and the shape of the guide wire can not be accurately understood in the monitor image of the MRI.

Example 12

The guide wire shown in FIG. 11 is manufactured. Each of the conditions of the guide wire is as follows.

TOTAL LENGTH OF GUIDE WIRE: 1500 mm

WIRE MAIN BODY: WIRE MATERIAL (CORE MEMBER) HAVING SOLID CIRCULAR CROSS SECTION

MATERIAL CONSTITUTING WIRE MAIN BODY: SUPERELASTIC ALLOY (Ni-49 wt % Ti ALLOY)

OUTER DIAMETER OF WIRE MAIN BODY: 0.5 mm

COMPOSITION OF THIN FILM: Ni

SHAPE OF THIN FILM: RING SHAPE

DIMENSION OF THIN FILM: WIDTH; 2 mm, THICKNESS; 0.05 $\mu$m

POSITION OF FORMING THIN FILM: POSITION AT WHICH CENTER OF THIN FILM IN WIDTH DIRECTION IS 3 mm FROM FRONT END OF WIRE MAIN BODY

METHOD OF FORMING THIN FILM: VACUUM EVAPORATION

Example 13

The guide wire having the same structure as that of the Example 12 except that the conditions for the thin film is changed as follows is manufactured.

COMPOSITION OF THIN FILM: Ni—Co—Cr—Al—Cu ALLOY

SHAPE OF THIN FILM: RING SHAPE

DIMENSION OF THIN FILM: WIDTH W=2 mm, THICKNESS=0.05 $\mu$m

POSITION OF FORMING THIN FILM: POSITION AT WHICH CENTER OF THIN FILM IN WIDTH DIRECTION IS 3 mm FROM FRONT END OF WIRE MAIN BODY

METHOD OF FORMING THIN FILM: SPUTTERING

Example 14

The guide wire having the structure shown in FIG. 12 is manufactured by forming a coated layer in accordance with the following conditions on the guide wire having the same structure as that of the Example 12.

FORMING AREA OF COATED LAYER: AREA EXTENDING SUBSTANTIALLY ALL THE LENGTH OF GUIDE WIRE

RESIN COMPOSITION OF COATED LAYER: POLYURETHAINE

X-RAY IMPERMEABLE MATERIAL IN COATED LAYER: ADDING TUNGSTEN (W) OF 45 wt %

THICKNESS OF COATED LAYER: 0.2 mm

Example 15

The guide wire having the structure shown in FIG. 12 is manufactured by forming the same coated layer as that of the Example 14 on the guide wire having the same structure as that of the Example 13.

Example 16

The guide wire shown in FIG. 13 is manufactured. Each of the conditions of the guide wire is as follows.

TOTAL LENGTH OF GUIDE WIRE: 1500 mm

WIRE MAIN BODY: WIRE MATERIAL (CORE MEMBER) HAVING SOLID CIRCULAR CROSS SECTION

MATERIAL CONSTITUTING WIRE MAIN BODY: SUPERELASTIC ALLOY (Ni-49 wt % Ti ALLOY)

OUTER DIAMETER OF WIRE MAIN BODY: 0.5 mm

OUTER DIAMETER OF NARROW DIAMETER PORTION IN FRONT END OF WIRE: 0.16 mm

COMPOSITION OF THIN FILM: Ni

SHAPE OF THIN FILM: RING SHAPE (THREE)

DIMENSION OF THIN FILM: WIDTH W=2 mm, THICKNESS 0.05 $\mu$m, DISTANCE BETWEEN GAPS L=8 mm

POSITION OF FORMING THIN FILM: RANGE BETWEEN 5 AND 35 mm FROM FRONT END OF WIRE MAIN BODY

METHOD OF FORMING THIN FILM: ELECTROLESS PLATING

RESIN COMPOSITION OF COATED LAYER: POLYURETHANE

X-RAY IMPERMEABLE MATERIAL IN COATED LAYER: ADDING TUNGSTEN (W) OF 45 wt %

THICKNESS OF COATED LAYER (AVERAGE): 0.2 mm

Comparative Example 3

The guide wire having the same structure as that of the Example 12 except that the material constituting the wire main body is set to be a stainless steel (SUS304, magnetic susceptibility: 15.23×10$^{-4}$) and no thin film is provided is manufactured.

Comparative Example 4

The guide wire having the same structure as that of the Example 16 except that no thin film is provided is manufactured.

<Experiment>

With respect to the case of placing each of the guide wires in accordance with the Examples 12 to 16 and the comparative Examples 3 and 4 into a water, an MRI image thereof is monitored by using an MRI (manufactured by GE MEDICAL CO., LTD) and photographing by a gradient echo method.

Figure 14:
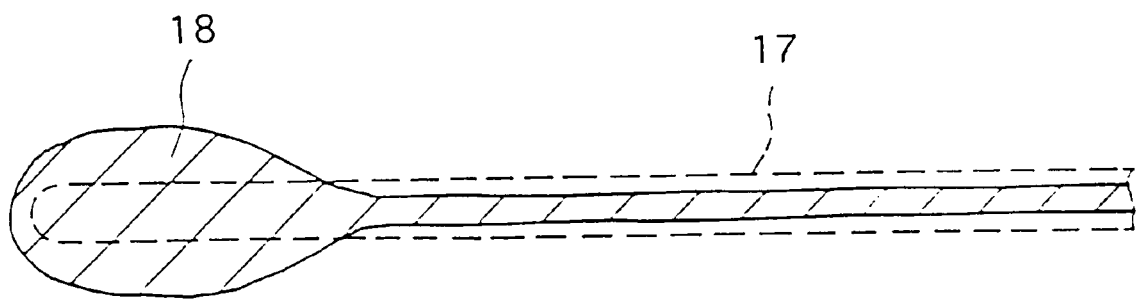
FIG. 14 is a schematic view which shows an outer appearance of a guide wire and a shape of an artifact of a guide wire on an MRI image in accordance with the present invention.

In each of the guide wires in accordance with the Examples 12 to 15, a contour 17 of the actual guide wire (a dot line in FIG. 14) and an artifact 18 of the guide wire present on the MRI image (a solid line in FIG. 14) become shapes shown in FIG. 14 (schematically shown).

Figure 15:
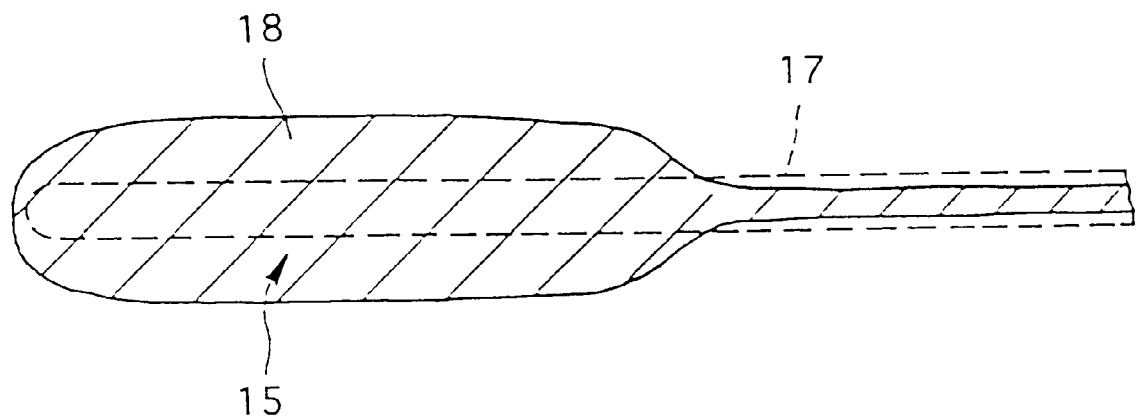
FIG. 15 is a schematic view which shows an outer appearance of a guide wire and a shape of an artifact of a guide wire on an MRI image in accordance with the present invention.

Further, in each of the guide wire in accordance with the Example 16, the contour 17 of the actual guide wire (a dot line in FIG. 15) and the artifact 18 of the guide wire present on the MRI image (a solid line in FIG. 15) become shapes shown in FIG. 15 (schematically shown).

Figure 16:
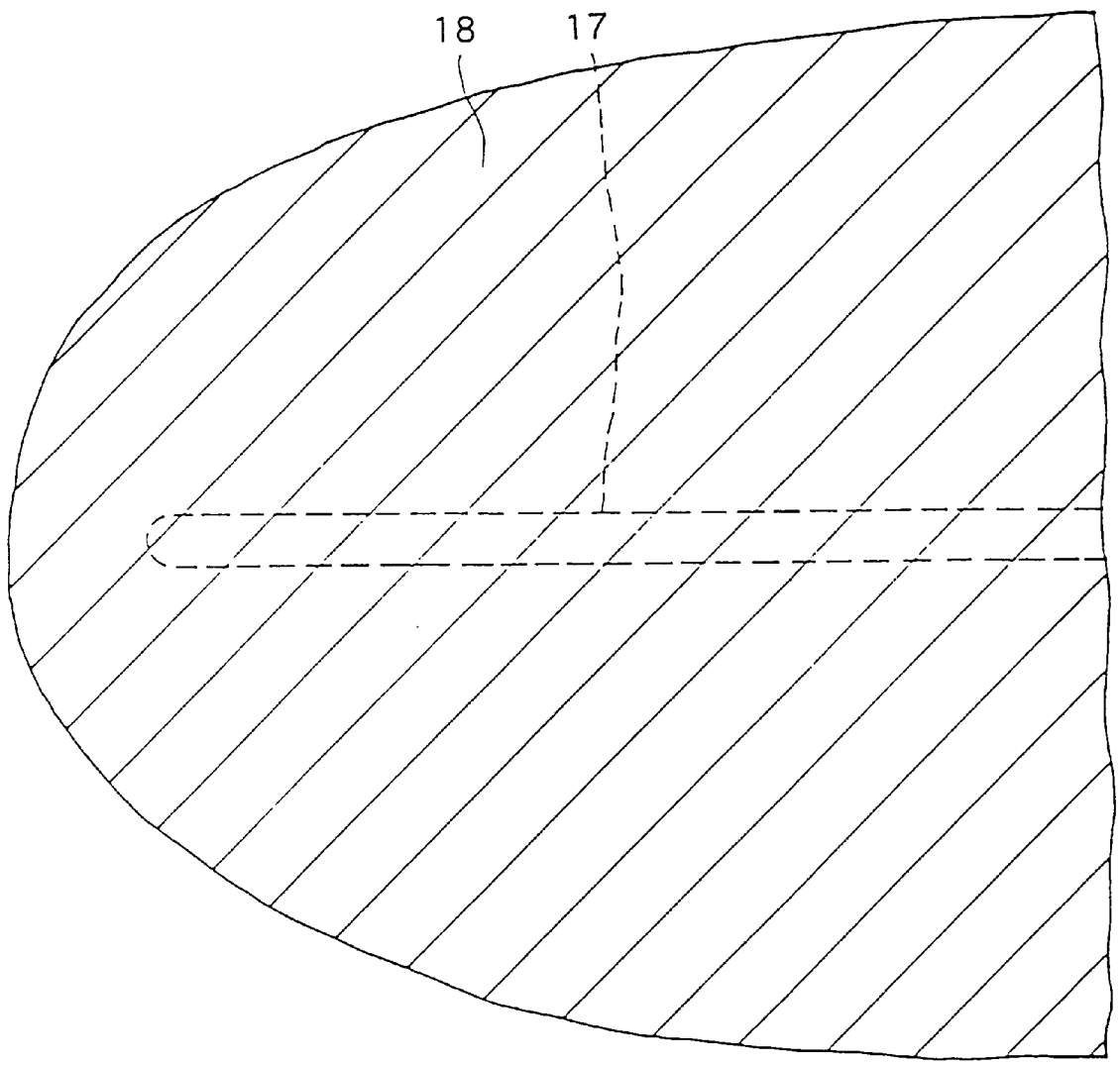
FIG. 16 is a schematic view which shows an outer appearance of a guide wire and a shape of an artifact of a guide wire on an MRI image in accordance with a comparative example.

On the contrary, in the guide wire in accordance with the comparative Example 3, the contour 17 of the actual guide wire (a dot line in FIG. 16) and the artifact 18 of the guide wire present on the MRI image (a solid line in FIG. 16) become shapes shown in FIG. 16 (schematically shown).

Figure 17:
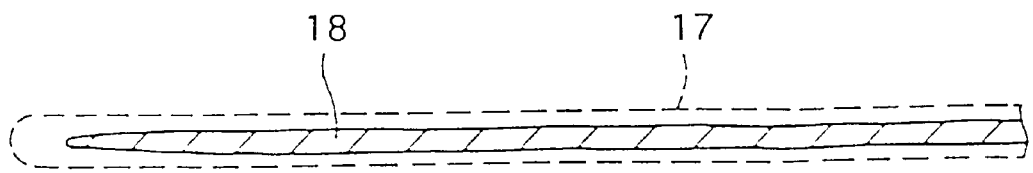
FIG. 17 is a schematic view which shows an outer appearance of a guide wire and a shape of an artifact of a guide wire on an MRI image in accordance with a comparative example.

Further, in the guide wire in accordance with the comparative Example 4, the contour 17 of the actual guide wire (a dot line in FIG. 17) and the artifact 18 of the guide wire present on the MRI image (a solid line in FIG. 17) become shapes shown in FIG. 17 (schematically shown). In this case, the artifact is very unclear particularly in the front end thereof and is hard to be recognized.

A magnification (an average value in each portion) of the artifact with respect to the actual outer diameter of the contrast portion in the guide wire is measured from the MRI image, so that the following results can be obtained.

Example 12: 6.6 times

Example 13: 6.0 times

Example 14: 3.7 times

Example 15: 3.3 times

Example 16: 1.2 times

Comparative Example 3: 25.6 times

Comparative Example 4: 0.5 times

Due to the results mentioned above, in each of the guide wires in accordance with the Examples 12 to 16, a position of the guide wire, particularly a position of the front end portion and a shape of the guide wire can be more accurately understood in the monitor image of the MRI.

In comparison with this, in the guide wire in accordance with the comparative Example 3, the artifact appears significantly greater than the actual outer diameter of the guide wire, and in the guide wire in accordance with the comparative Example 4, the image of the guide wire is unclear, so that in any of the cases, the position and the shape of the guide wire can not be accurately understood in the monitor image of the MRI.

<Experiment>

With respect to each of the guide wires in accordance with the Examples 14 to 16, the image is monitored under the X-ray illumination in accordance with a fixed method, so that in any of the guide wires, the total shape thereof or the position of the front end portion can be accurately understood in the monitor image of the MRI.

As mentioned above, in accordance with the guide wire of the invention, the position and the shape of the guide wire can be appropriately recognized by the monitor image by means of the MRI.

Accordingly, in the case of performing the medical activity such as the examination, the diagnosis and the treatment with using the guide wire of the invention under monitoring by the MRI, the medical activity can be smoothly and suitably performed.

Particularly, in accordance with the invention, a magnitude of the artifact with respect to the actual outer diameter of the guide wire and a portion in which the artifact is generated can be suitably adjusted by setting the conditions such as the composition of the thin film, the size, the formed position and the formed pattern, so that a desired characteristic can be easily obtained.

What is claimed is:

1. A guide wire for MRI comprising a contrast portion generating an artifact one to eight times an actual diameter of an MRI image photographed by a gradient echo method, said contrast portion having an organic coating layer of 0.05 mm–0.3 mm thickness coating at least a part of said contrast portion.

2. A guide wire as recited in claim 1, wherein said contrast portion is present in at least a front end portion of the guide wire.

3. A guide wire as recited in claim 1, wherein said contrast portion is made of an alloy containing a nickel of 40 wt % or more and an iron of 7 wt % or less.

4. A guide wire as recited in claim 3, wherein said alloy further contains a chrome and a molybdenum.

5. A guide wire as recited in claim 4, wherein said alloy contains a nickel of 45 wt % or more, an iron of 2 to 7 wt %, a chrome of 10 to 25 wt % and a molybdenum of 10 to 20 wt %.

6. A guide wire as recited in claim 1, wherein said coating layer is constituted by an organic polymeric layer.

7. A guide wire as recited in claim 1, including a core member constituted by a metal material having a magnetic susceptibility of $0.5\times10^{-4}$ to $5.0\times10^{-4}$ in an outer diametrical direction at a temperature close to room temperature.

* * * * *